US00PP21464P3

(12) United States Plant Patent

Hanna et al.

(10) Patent No.: US PP21,464 P3

(45) Date of Patent: Nov. 9, 2010

(54) *PENNISETUM* PLANT NAMED 'TIFT-17'

(50) Latin Name: ***Pennisetum purpureum*×[*Pennisetum glaucum*×(*Pennisetum purpureum*×*Pennisetum squamulatum*)]**

Varietal Denomination: Tift-17

(75) Inventors: Wayne William Hanna, Chula, GA (US); S. Kristine Braman, Griffin, GA (US)

(73) Assignee: University of Georgia Research Foundation, Athens, GA (US)

( * ) Notice: Subject to any disclaimer, the term of this patent is extended or adjusted under 35 U.S.C. 154(b) by 0 days.

(21) Appl. No.: 12/378,547

(22) Filed: Feb. 17, 2009

(65) Prior Publication Data

US 2010/0212053 P1 Aug. 19, 2010

(51) Int. Cl.
*A01H 5/00* (2006.01)

(52) U.S. Cl. ..... Plt./384

(58) Field of Classification Search ..... Plt./384
See application file for complete search history.

(56) References Cited

U.S. PATENT DOCUMENTS

PP17,728 P3 5/2007 Hanna et al.
PP18,509 P3 2/2008 Hanna et al.

OTHER PUBLICATIONS

Hanna, Wayne, William, U.S. Appl. No. 12/378,553, filed Feb. 17, 2009, *Pennisetum* 'Tift-23', 9 pages.

*Primary Examiner*—June Hwu
(74) *Attorney, Agent, or Firm*—Davis Wright Tremaine LLP

(57) ABSTRACT

The new variety *Pennisetum* 'Tift-17' is provided. The new and distinct variety has excellent drought tolerance; superior *Helminthosporium* leaf spot resistance; high ornamental value; higher tiller number in drought conditions; cold tolerance for short periods of time; and relatively long trichomes on the sheath and at the leaf blade edge at the collar. The asexually reproduced variety is reliably propagated vegetatively.

1 Drawing Sheet

Latin name of the genus and species of the plant claimed: 'Tift-17' is a tri-specific ornamental *Pennisetum hybrid* of the genus and species *Pennisetum purpureum*×*[Pennisetum glaucum*×(*Pennisetum purpureum*×*Pennisetum squamulatum*)].

Variety denomination: The new *Pennisetum* claimed is of the variety denominated 'Tift-17'.

BACKGROUND OF THE INVENTION

The present invention relates to a new and distinct cultivar of *Pennisetum* botanically known as *Pennisetum purpureum*× *[Pennisetum glaucum*×(*Pennisetum purpureum*×*Pennisetum squamulatum*)], and herein referred to as 'Tift-17'.

The new *Pennisetum* is a product of a planned breeding program conducted by the Inventors in Tifton, Ga. The objective of the *Pennisetum* breeding program is to create new plant cultivars with improved commercial qualities. This cultivar is commercially important for its superior ornamental value. The baseline ornamental value increases during drought stress. These and other qualities are enumerated herein.

Pedigree and history: In 2003, red tetraploid (2n=4x=28) pearl millet (unpatented *Pennisetum glaucum,* designated '04-94') was crossed with SC 1125-2 [a Merkeron napiergrass (unpatented *P. purpureum;* 2n=4x=28) that had been crossed with PS 262 (unpatented *P. squamulatum,* 2n=8x=56)]. One vigorous plant from the SC 1125-2/PS 262 cross, designated '04-26-1', was selected in 2004. In 2004, 'Princess' napiergrass (patented: U.S. Plant Pat. No. 17,728; 2n=4x=28, female parent) was pollinated with unpatented '04-26-1' (male parent). The new variety 'Tift-17' was the seventeenth plant selected in 2005 from the 2004 cross. The new variety 'Tift-17' has been tested since 2005.

Asexual reproduction of the new variety *Pennisetum* 'Tift-17' by vegetative propagation (single stem propagules) in a controlled environment in Tifton, Blairsville and Griffin, Ga. since 2005, has shown that the unique features of this new *Pennisetum* are stable and reproduced true to type in successive generations.

SUMMARY OF THE INVENTION

The new variety *Pennisetum* 'Tift-17' has not been observed under all possible environmental conditions. The phenotype may vary somewhat with variations in environment and cultural practices such as temperature and light intensity without, however, any variance in genotype.

The following traits have been repeatedly observed in Tifton and Griffin Ga., and are determined to be the unique characteristics of the new variety 'Tift-17':

1. Excellent drought tolerance;
2. Superior *Helminthosporium* leaf spot resistance;
3. High ornamental value and maintains value under drought conditions;
4. High tiller number in drought conditions;
5. Cold tolerant for short periods of time;
6. Relatively long trichomes on the sheath and at the leaf blade edge at the collar.

The new variety *Pennisetum* 'Tift-17' can be compared to its parents, 'Princess' and '04-26-1', and other grasses developed by University of Georgia researchers, such as the patented (U.S. Plant Pat. No. 18,509) *Pennisetum* 'Prince' and co-pending plant patent application for 'Tift-23' ( U.S. Plant patent application Ser. No. 12/378,553), filed on the same date as the instant application.

Comparison to female parent 'Princess'. The new variety 'Tift-17' is similar in height, plant base diameter, leaf width, and non-drought tiller number to its parent 'Princess'. The new variety 'Tift-17' has longer leaf length compared to 'Princess'. Tiller number when grown in drought conditions is higher for the new variety 'Tift-17' than 'Princess', and the new variety 'Tift-17' produced a much more desirable plant type. The new variety 'Tift-17' rated a significantly higher ornamental value than 'Princess' in all tests, including two of three tests for color. Field trials indicate that the new variety 'Tift-17' has improved resistance to *Helminthosporium* leaf spot as compared to 'Princess'. Lastly, the new variety 'Tift-17' produced a significantly wider plant canopy than 'Princess'.

Comparison to male parent '04-26-1'. The new variety 'Tift-17' is similar in leaf length, leaf collar trichome length, disease resistance, and approximately the same in abaxial leaf color as parent '04-26-1'. The new variety 'Tift-17' is slightly different from parent '04-26-1' in adaxial leaf color [the new variety 'Tift-17' is mottled Greyed-purple RHS 187D whereas '04-26-1' is mottled Grey-purple RHS 183B and Brown-green 138A with each color individually present in the leaf]. The new variety 'Tift-17' has significantly longer trichomes on the leaf blade edge at the collar, is shorter in height, and wider in leaf width than parent '04-26-1'. The new variety 'Tift-17' has sheath trichomes whereas '04-26-1' does not have sheath trichomes. The new variety 'Tift-17' is a perennial at Tifton, Ga. whereas '04-26-1' is a weak perennial at Tifton, Ga. The new variety 'Tift-17' has no flowers in late October in Tifton, Ga. whereas '04-26-1' has flowers in late October in Tifton, Ga. Lastly, the new variety 'Tift-17' has a different midrib color: The new variety 'Tift-17' is about Greyed-purple RHS 187B, and '04-26-1' is about Red-purple RHS 61C.

Comparison to 'Prince' The new variety 'Tift-17' is significantly shorter than 'Prince'. Leaf length of the new variety 'Tift-17' is significantly shorter than that of 'Prince'. The new variety 'Tift-17' rated a significantly higher ornamental value than 'Prince' in all tests, including two of three tests for color. Field trials indicate that the new variety 'Tift-17' has improved resistance to *Helminthosporium* leaf spot as compared to 'Prince'.

Comparison to 'Tift-23'. The new variety 'Tift-17' is approximately 60% taller, has longer and wider leaves, has unmottled leaves, has longer trichomes on the leaf blade edge at the collar, with those trichomes placed further away from the collar, and has sheath trichomes whereas 'Tift-23' does not. The new variety 'Tift-17' is otherwise similar to 'Tift-23' in that it has similar abaxial leaf color, midrib color, has no trichomes on either leaf surface, is cold tolerant and disease resistant, and does not flower in late October.

BRIEF DESCRIPTION OF THE FIGURES

The accompanying photographic illustration shows typical specimens in full colour of the foliage of the new variety *Pennisetum* 'Tift-17'. The colors are as nearly true as is reasonably possible in a color representation of this type.

BOTANICAL DESCRIPTION

Figure 1:
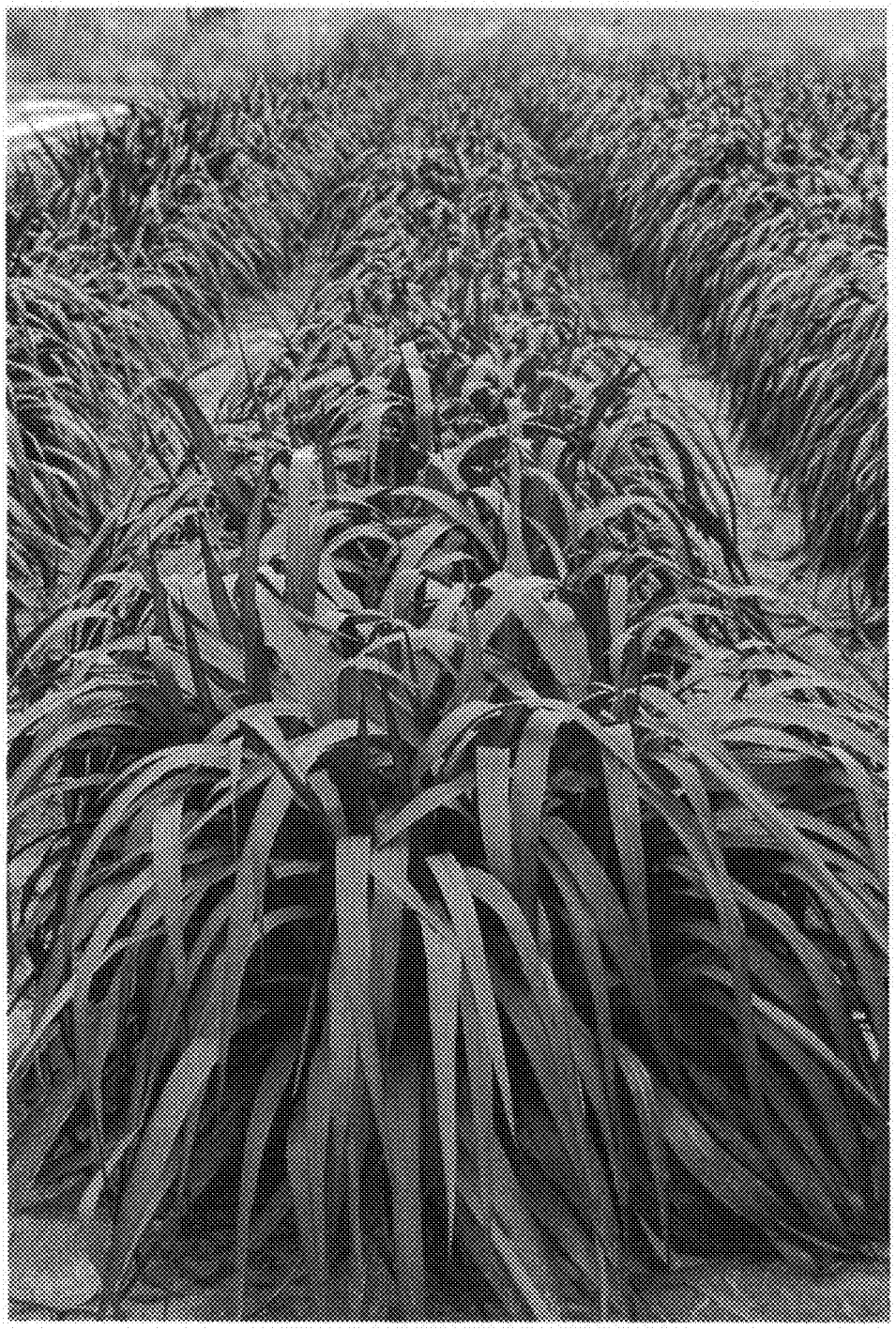
FIG. 1 is a photograph of the new variety *Pennisetum* 'Tift-17'.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England.

The following observations, measurements and values describe plants grown in Tifton, Blairsville, or Griffin, Ga. During the growing of the plants, day temperatures ranges from approximately 50° F. to approximately 99° F. and night temperatures ranges from approximately 20° F. to approximately 70° F.

The new variety 'Tift-17' is a perennial at Tifton, Ga. (U.S.D.A. zone 8a). The new variety 'Tift-17' survived at approximately 20° F. for one night in the field during the 2007/2008 winter at Tifton, but did not survive the 2006/2007 winters at Griffin or Blairsville, nor the 2007/2008 winter at Blairsville. Because of its vigor, it can effectively be used as an annual where it will not survive freezing temperatures in the winter.

The new variety 'Tilt-17' is pollen and seed sterile and does not produce seed heads at Tifton, Ga. in the field.

All data are from plants established as single stem propagules in mid-May, and rated in September through October. Plants were spaced at 2 meter centers. Color indicators are according to The Royal Horticultural Society (R.H.S.) Colour Chart, 5$^{th}$ Edition.

Other data are as follows:

Mature plant height: Approximately 72-140 cm.
Culm: Approximately 74 cm long for plants that are 150 days old; completely covered by leaf sheath.
Diameter of plant canopy: Approximately 133-160 cm.
Diameter of base: Approximately 22-48 cm.
Leaf width: Approximately 30-33 mm.
Leaf length: Approximately 61-83 mm.
Leaf apex shape: Apiculate, ending in a sharp point.
Adaxial leaf surface trichomes: None.
Abaxial leaf surface trichomes: None.
Leaf blade margin trichome length: <0.1 mm.
Leaf collar trichome length: Approximately 3 mm.
Leaf blade edge at collar trichome: Approximately 6 mm long for about 6 mm from collar.
Ligule: No membranous ligule present; lined with trichomes.
Sheath trichomes: Approximately 2 mm long for about 2 cm from collar.
Number of tillers: Approximately 38-65, decreasing with drought.
Adaxial leaf color: About greyed-purple RHS 187D.
Abaxial leaf color: About greyed-purple RHS 187D.
Midrib color: About greyed-purple RHS 187D.
Inflorescence: None.

What is claimed is:

1. A new and distinct variety of the *Pennisetum* plant named 'Tift-17', substantially as illustrated and described herein.

* * * * *